(12) United States Patent
Emery et al.

(10) Patent No.: US 7,887,494 B2
(45) Date of Patent: Feb. 15, 2011

(54) FLUID SAMPLE TRANSPORT DEVICES AND METHODS

(75) Inventors: Jeffrey Lorne Emery, Redwood City, CA (US); Jeffrey M. Jones, Sunnyvale, CA (US); Raul Escutia, Palo Alto, CA (US); Stephen Mark Yee, Sunnyvale, CA (US)

(73) Assignee: Intuity Medical, Inc., Sunnyvale, CA (US)

( * ) Notice: Subject to any disclaimer, the term of this patent is extended or adjusted under 35 U.S.C. 154(b) by 696 days.

(21) Appl. No.: 11/239,094

(22) Filed: Sep. 30, 2005

(65) Prior Publication Data

US 2007/0078313 A1    Apr. 5, 2007

(51) Int. Cl.
*A61B 5/00* (2006.01)
*A61B 5/05* (2006.01)

(52) U.S. Cl. .................. 600/584; 600/309; 600/345; 600/347; 600/365; 600/573; 600/583

(58) Field of Classification Search .................. 600/573
See application file for complete search history.

(56) References Cited

U.S. PATENT DOCUMENTS

| | | | |
|---|---|---|---|
| 4,846,785 A * | 7/1989 | Cassou et al. ................. | 600/34 |
| 5,746,217 A | 5/1998 | Erickson et al. | |
| D403,975 S | 1/1999 | Douglas et al. | |
| 5,911,711 A | 6/1999 | Pelkey | |
| 5,951,492 A * | 9/1999 | Douglas et al. ............. | 600/583 |
| 5,962,215 A * | 10/1999 | Douglas et al. ................ | 435/4 |
| 6,058,321 A | 5/2000 | Swayze et al. | |
| 6,162,639 A | 12/2000 | Douglas | |
| 6,271,045 B1 | 8/2001 | Douglas et al. | |
| 6,455,324 B1 | 9/2002 | Douglas | |
| 6,544,475 B1 | 4/2003 | Douglas et al. | |
| 6,602,205 B1 * | 8/2003 | Erickson et al. ............. | 600/573 |
| 6,612,111 B1 * | 9/2003 | Hodges et al. ................ | 60/583 |
| 2003/0135333 A1 * | 7/2003 | Aceti et al. ................... | 702/31 |
| 2004/0096959 A1 | 5/2004 | Stiene et al. | |
| 2007/0078358 A1 | 4/2007 | Escutia et al. | |

FOREIGN PATENT DOCUMENTS

| | | |
|---|---|---|
| EP | 0 396 016 A2 | 11/1990 |
| EP | 1 529 489 A1 | 5/2005 |
| WO | WO 96/25088 A1 | 8/1996 |
| WO | WO 02/082052 A2 | 10/2002 |

OTHER PUBLICATIONS

U.S. Appl. No. 11/529,614, filed Sep. 29, 2006, Jeffrey Lorne Emery et al.
U.S. Appl. No. 11/529,613, filed Sep. 29, 2006, Raul Escutia et al.
U.S. Appl. No. 11/529,612, filed Sep. 29, 2006, Raul Escutia et al.
International Search Report and Written Opinion of the International Searching Authority dated Mar. 26, 2007, issued in connection with the corresponding International application.

* cited by examiner

*Primary Examiner*—Patricia Mallari
(74) *Attorney, Agent, or Firm*—Buchanan Ingersoll & Rooney PC

(57) ABSTRACT

Arrangements are provided including a fluid transport tube, or a needle, having a first end and a second end opposite the first end, and a lumen having an inner diameter. At least one fluid transport enhancing projection is disposed in the lumen and extends from the second end toward the first end. A discreet, wearable blood glucose monitor including such arrangements is also described.

52 Claims, 8 Drawing Sheets

FLUID SAMPLE TRANSPORT DEVICES AND METHODS

FIELD OF THE INVENTION

The presented invention is directed to devices, arrangements and associated methods for effectively transporting fluids, for example, samples of body fluids.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

According to the American Diabetes Association, diabetes is the fifth-deadliest disease in the United States and kills more than 213,000 people a year, the total economic cost of diabetes in 2002 was estimated at over $132 billion dollars, and the risk of developing type I juvenile diabetes is higher than virtually all other chronic childhood diseases.

In certain medical treatment and diagnostic procedures, it is necessary to transport body fluid from the patient to a remote location. For example, one such procedure is the testing of a sample of body fluid, such as blood for the glucose concentration level contained therein. Such diagnostic procedures may be conducted clinically or by the patient utilizing a self-testing device or arrangement. There are numerous devices and systems designed to be utilized by the patient for obtaining a sample of blood, and testing the sample to determine the glucose content at a particular point in time. One such system generally includes at least three separate devices. The first device is utilized to draw a sample of blood from the patient by performing a lancing or similar skin piercing operation. Lancets are solid members which do not include a pathway for transporting the sample of blood. Since the lancets do not offer the ability to transport the sample, a separate member or component must be provided for this purpose. Typically, such systems include a separate test strip member which is manually brought into contact with the sample of blood produced by the lancing operation. The sample is then introduced onto the test strip, which includes a mechanism, such as a chemical reagent, for reacting with the blood sample and producing a readable signal. To this end, a separate meter or other reading device is also included in the system. The test strip is typically introduced into the meter, which then interacts with the test strip to produce the quantification of the glucose content contained in the sample of blood.

Such systems suffer from certain drawbacks. The manual operations of lancing, bringing the test strip into contact with the sample of blood thus produced, and the separate step of inserting the test strip into the meter may be difficult to perform for some patients. For instance, diabetics often times suffer from visual impairment as a result of their condition. Thus, it may be difficult for them to locate the sample of blood on the surface of the skin and bring the test strip into communication therewith. Similarly, it may be difficult to properly insert the test strip into the meter. In addition, there is a trend toward minimizing the size of the lancet used to perform the lancing operation in an effort to minimize the pain and required blood volume for the meter associated with this self testing procedure, thereby promoting more frequent testing. The use of a smaller gauge lancet also results in a smaller volume of body fluid, or blood, produced by the lancing operation. Such smaller samples of blood may be even more difficult to locate by the patient, and also may be more challenging to transport effectively.

Other systems for self-testing on the market attempt to integrate one or more above-described lancing, transporting and quantification operations. One such system requires the user to load a lancet and a test strip into a device, which includes a meter. Once loaded the device is held against the skin and the test initiated by the user, which includes a lancing operation and subsequent transport of a sample of body fluid into the test strip. This arrangement still requires the manual step of loading a separate lancet and test strip correctly into the device, and orienting the device correctly at the surface of the skin in order to perform each test. This device also uses the lancet, which in and of itself does not provide a mechanism to transport the sample of blood. Thus, it is necessary to provide a separate mechanism, which enables transportation of the blood from the surface of the skin to the test strip. In this particular device, the transport function is performed by automatically moving the test strip, which includes capillary channels, into communication with the sample of blood at the surface of the skin. If the test strip is not loaded correctly, or the mechanisms for moving the test strip into position do not function correctly, the device will not function properly. Moreover, the user must purchase, store, handle and load the separate lancet and test strip components for each test. Thus, the successful performance for each test is again at least partially dependent upon the patient correctly associating the lancet and the test strip with the device for each and every test performed.

Yet another conventional self-testing system includes multiple disposable parts for lancing and analyte quantification. In this particular device, a test strip is provided which has an integrated blood transport member in the form of a capillary tube extending from a major planar surface thereof which must be brought into communication with the droplet of blood formed on the surface of the skin resulting from a lancing operation. In order to facilitate the transport function, the test strip is provided with a separate spreading layer sandwiched between the end of the capillary tube and a reagent membrane disposed on an opposing side thereof. The spreading layer facilitates transfer of the blood from the tube to the reagent layer. This system is designed such that a sample volume that completely fills the tube is required in order to obtain an accurate test result. Thus, approximately two micro liters of blood is typically required to be drawn from the patient such that the tube can be completely filled and transferred for further analysis. This requires creation of a wound in the skin large enough to express the necessary volume of blood, thus limiting lancet size reduction efforts, and perhaps increasing the manual milking of the wound to bring an adequate volume of blood to the surface of the skin of the patient. Also, the process of completely filling the tube is time consuming. This design also requires the blood to flow through the spreading layer prior to reaching the reagent layer. This two-layer structure is less than optimal from an assembly standpoint in that it requires the assembly of multiple distinct layers. Since the volume of the capillary tube must be first transferred through the spreading layer, this may also have a tendency to slow down the testing procedure and reduce the volume of sample available for analysis.

Thus, conventional body fluid transport systems for medical treatment and/or diagnostic procedures suffer certain drawbacks. Such drawbacks include transport operations that are reliant upon the dexterity and ability of the patient to accurately perform various manual procedures. The conventional devices and arrangements also are not fully integrated and require significant intervention on the part of the user in order to perform an accurate test.

SUMMARY OF THE INVENTION

It is, therefore, an object of this invention to provide devices, arrangements and methods for improved transport of a body fluid, such as blood.

According to the current principles of the present invention, one or more of the following advantages may be derived from such devices, arrangements and methods. Consistent with the principles of the present invention, a body fluid can be transported without the necessity of performing various operations or procedures by the patient or user of the device. Thus, for example, it is unnecessary for the patient or user of the device to manually bring a fluid member in communication with a droplet of blood on the surface of skin.

According to the present invention, it is also unnecessary to provide a body fluid sample having a volume at least large enough to fill a capillary tube or other fluid transport member, thus reducing the time necessary to perform a test as well as providing an opportunity to create a smaller wound in the surface of the skin, thereby minimizing pain associated with a lancing or other wound creating procedure.

According to the principles of the current invention improved fluid transport can be provided by associating fluid transport with a fully integrated device. A fully integrated device formed according to the principles of the present invention provides for a potential lower cost device due to a reduction in distinct components which may be sourced from different vendors, which may provide a reduced manufacturing burden (i.e. reduced packaging, assembly, etc.). According to the present invention, a needle serves multiple purposes, namely as a lancet and a transfer tube, all in a single device. This insures that a sterile skin-piercing member is used for each and every test, thereby reducing the risk on infection and/or pain associated with lancet reuse, as well as simplified operation.

A further possible advantage provided by the present invention is the elimination of spreading/filtering media or layer. This advantage eliminates the reliance on a special spreading media which can reduce the volume of blood available to the reagent, thereby providing an opportunity for even greater sample volume reduction and related pain reduction. The elimination of a spreading/filtering media or layer also simplifies manufacturing, for example, by reducing the necessity of correctly positioning a small spreading media layer relative to other components of the assembly.

According to one aspect of the present invention, there is provided an arrangement comprising: a needle comprising a first end and a second end opposite the first end, and a lumen having an inner diameter; and at least one fluid transport enhancing projection disposed in the lumen of the needle and extending from the second end toward the first end.

According to a further aspect, the present invention provides an arrangement comprising: a base having a bore disposed therein extending from a first surface of the base through a second surface of the base; a fluid transport tube having a first end, a second end opposite the first end, and a lumen having an inner diameter, the second end of the tube being received within the bore of the base; at least one fluid transport enhancing projection disposed in the lumen of the tube and extending from the second end toward the first end; and an analyte quantification member in fluid communication with the bore.

According to yet another aspect, the present invention provides a wearable blood glucose monitor comprising any of the arrangements described herein.

BRIEF DESCRIPTION OF THE DRAWINGS

The preferred embodiments are illustrated in the drawings in which like reference numerals refer to the like elements and in which.

DETAILED DESCRIPTION OF THE INVENTION

Figure 1:
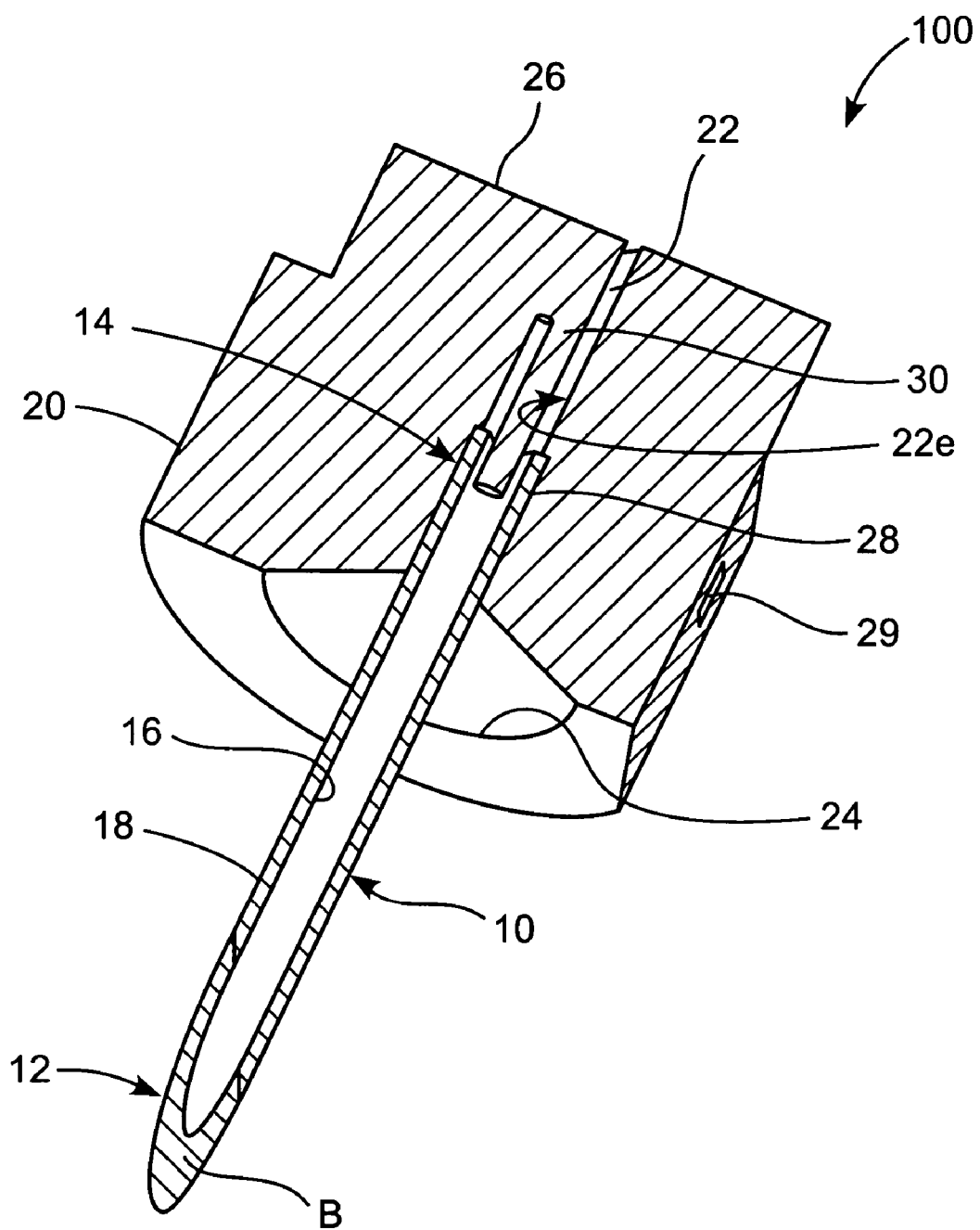
FIG. 1 is a cross sectional view of an arrangement formed according to the principles of the present invention.
Figure 2:
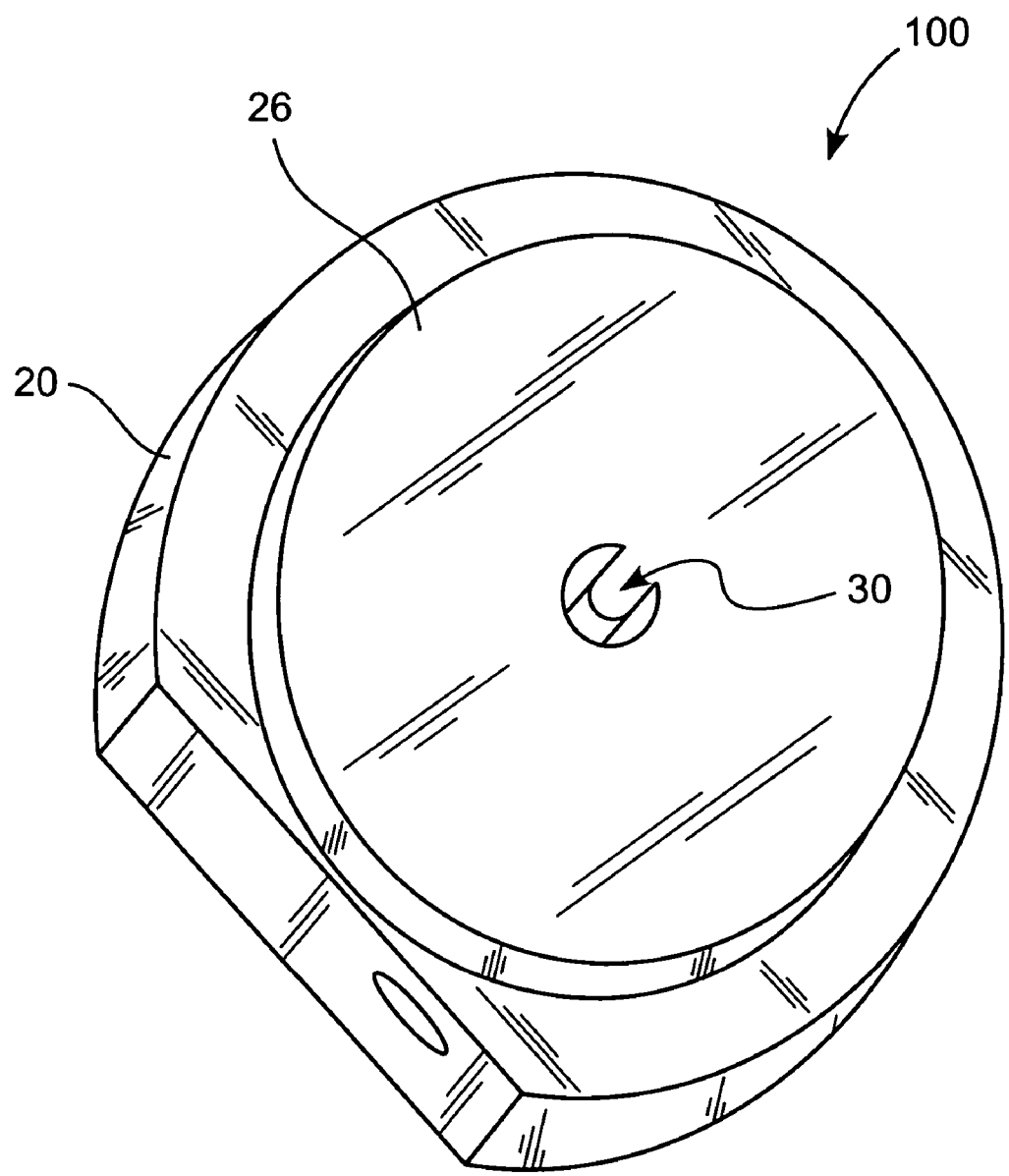
FIG. 2 is a top view of the arrangement of FIG. 1.
Figure 3:
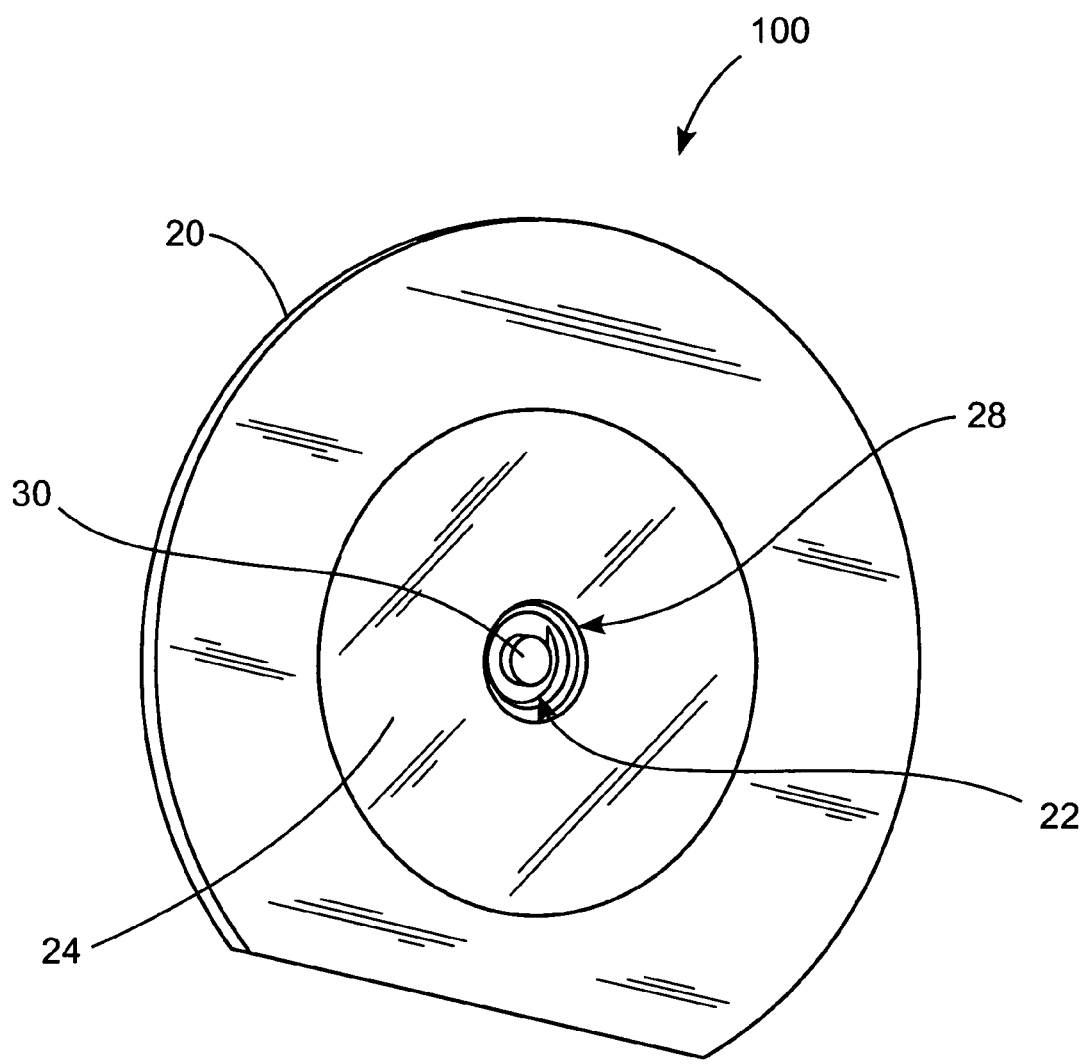
FIG. 3 is a bottom view of the arrangement of FIG. 1

Devices, arrangements and their associated methods are structured to comprise one or more of the following characteristics.

An exemplary arrangement 100 formed consistent with the principles of the present invention is illustrated in FIGS. 1-4. The arrangement 100 includes a fluid transport tube 10. The fluid transport tube 10 may be formed from any suitable material, such as a metal, glass, or polymeric material. The fluid transport tube 10 may be provided with an inner diameter that is sufficient to produce a capillary action of fluid flowing through the tube. By way of example, the fluid transport 10 may be provided with inner diameter on the order of 0.007 to 0.012 inches. The fluid transport 10 may be provided with a first end 12 and a second end 14 opposite the first end 12. A lumen 16 having an inner diameter, optionally dimensioned as described above, extends between the first end 12 and the second end 14. The lumen 16 may be provided, on at least on a portion of the surface thereof, with a fluid transport-enhancing feature. For example, such a feature may comprise a suitable coating, such as polydimethylsiloxane (PDMS) or Silwet™. Alternatively, at least a portion of the surface of lumen 16 may be provided with a surface texturing which promotes fluid flow, such as a surface roughening or pattern applied on at least a portion of the surface. According to one embodiment of the present invention, the fluid transport tube 10 is in a form of a needle 18. The first end 12 of the needle 18 is provided with a construction adapted to pierce the surface of the skin, such as bevel B or other configuration known in the art. The needle 18 may be provided with one or any combination of the features of the fluid transport tube, as described above.

The arrangement 100 may further include a base 20. The base 20 may have any suitable geometry or size. In the embodiment demonstrated in FIGS. 1-4, the base 20 can be in the form of a generally rounded hub. However, the base 20 of the present invention is not limited to this geometry, and in fact, as illustrated in other embodiments described herein, may have other suitable geometries. Base 20 is formed of any suitable material. For example, the base 20 can be formed of a metal or polymeric material. The base 20 may be provided with a bore 22 that extends from a first surface 24 of the base 20 and through a second surface 26. As illustrated, the base 20 receives at least the second end 14 of the fluid transport tube 10 or needle 18. According to one alternative embodiment, the base 20 may be further provided with a counter bore 28 for receiving the fluid transport tube 10 or needle 18 at the second end 14 thereof. According to one alternative embodiment, as illustrated in FIGS. 1-4, the bore 22 extends beyond the second end 14 of the fluid transport tube 10 or needle 18 before reaching the second surface of 26 the base 20. The above-described portion of the bore 22 is indicated at 22*e*. According to one embodiment of the present invention, the transition between the inner lumen 16 at the second end of the tube 10 or needle 18, and the bore 22, or portion 22*e* thereof, is as smooth as possible in order to minimize adverse impacts on capillary flow. Thus, the lumen 16 and the bore 22, or portion thereof 22*e*, may be formed with substantially the same inner diameter. In this context "substantially the same" is intended to encompass surface imperfections and irregularities attributable to the limitations of current common manufacturing techniques. According to a further alternative embodiment, the fluid transport 10 or needle 18 may be receive in the base 20 such that the second end 14 is substantially is co-planar with the second surface 26 of the base 20 (See, e.g., FIG. 5). The base optionally includes a recess or passageway 29 for accommodating an actuation member, like a spring, therein.

The arrangement 100 includes a fluid transport enhancing projection 30. The fluid transport enhancing projection 30 is located in the lumen 16 of the tube 10 or needle 18. The projection 30 preferably extends from the second end 16 toward the first end 14 of the tube 10 or needle 18. The distance that the projection 30 may extend into lumen 16, toward the first end 12 may vary widely according to the teachings of the present invention. For example, the projection 30 may extend from 0 to 100%, preferably 75%, of the longitudinal length of the tube 10 or needle 18; however, this projection should not go beyond the beveled surfaces B of a needle 18 such that it would interact with the skin during the lancing process. For a given lumen 16 inner diameter, the longer the projection 30 the smaller the volume of fluid needed to effect transport. Alternatively, according to the present invention the projection 30 may extend down into the portion of the bore indicated at 22*e*, but terminates before extending past the second end 14 of the tube 10 or needle 18 and into the lumen 16. In other words, according to this embodiment of the present invention, the projection 30 extends 0% of the longitudinal length of the lumen 16 of the tube 10 or needle 18.

The projection 30 may be provided in many different forms. For example, as illustrated in FIGS. 1-4, the projection 30 may be essentially an integral extension of the base 20. In this regard, the projection 30 may be formed as a separate member and then integrated with the base 20 by attachment thereto, such as by gluing, welding, etc. Alternatively, the extension 30 and base 20 may be a monolithic part formed by any suitable technique, such as computerized numerically controlled (CNC) machining, electrical discharge machining (EDM), or microinjection molding.

Figure 5:
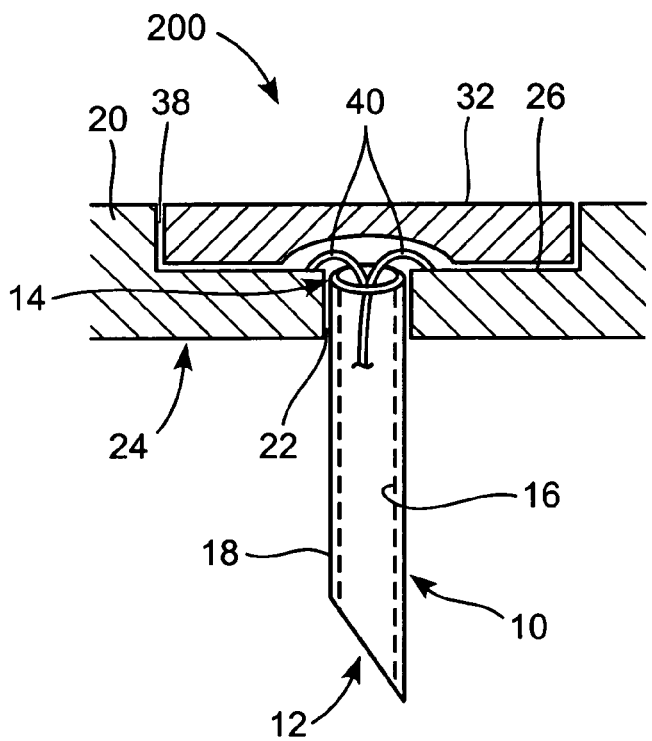
FIG. 5 is a partial cross sectional view of a further arrangement of the present invention.
Figure 7:
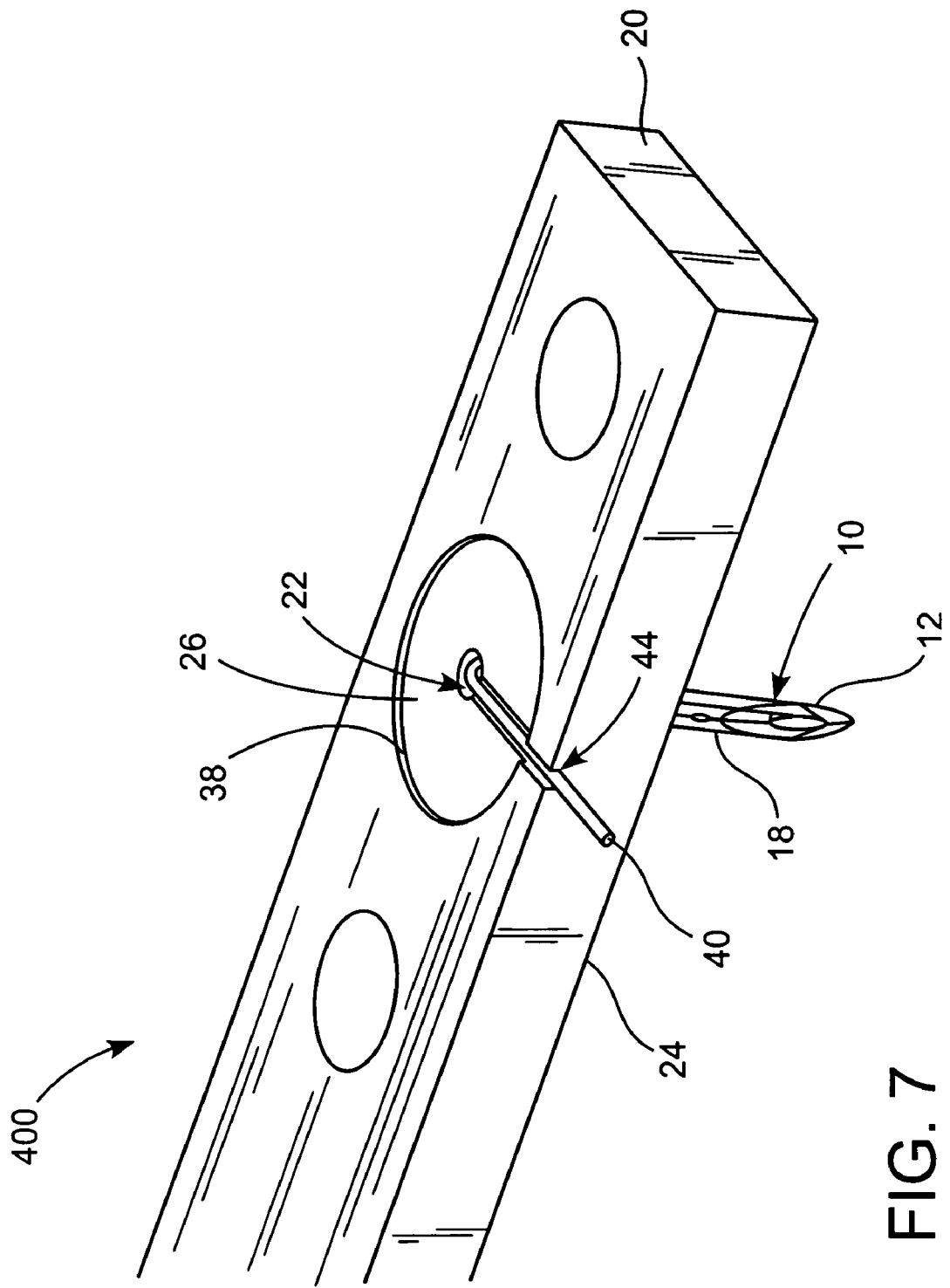
FIG. 7 is a perspective view of a further arrangement formed according to the present invention.
Figure 8:
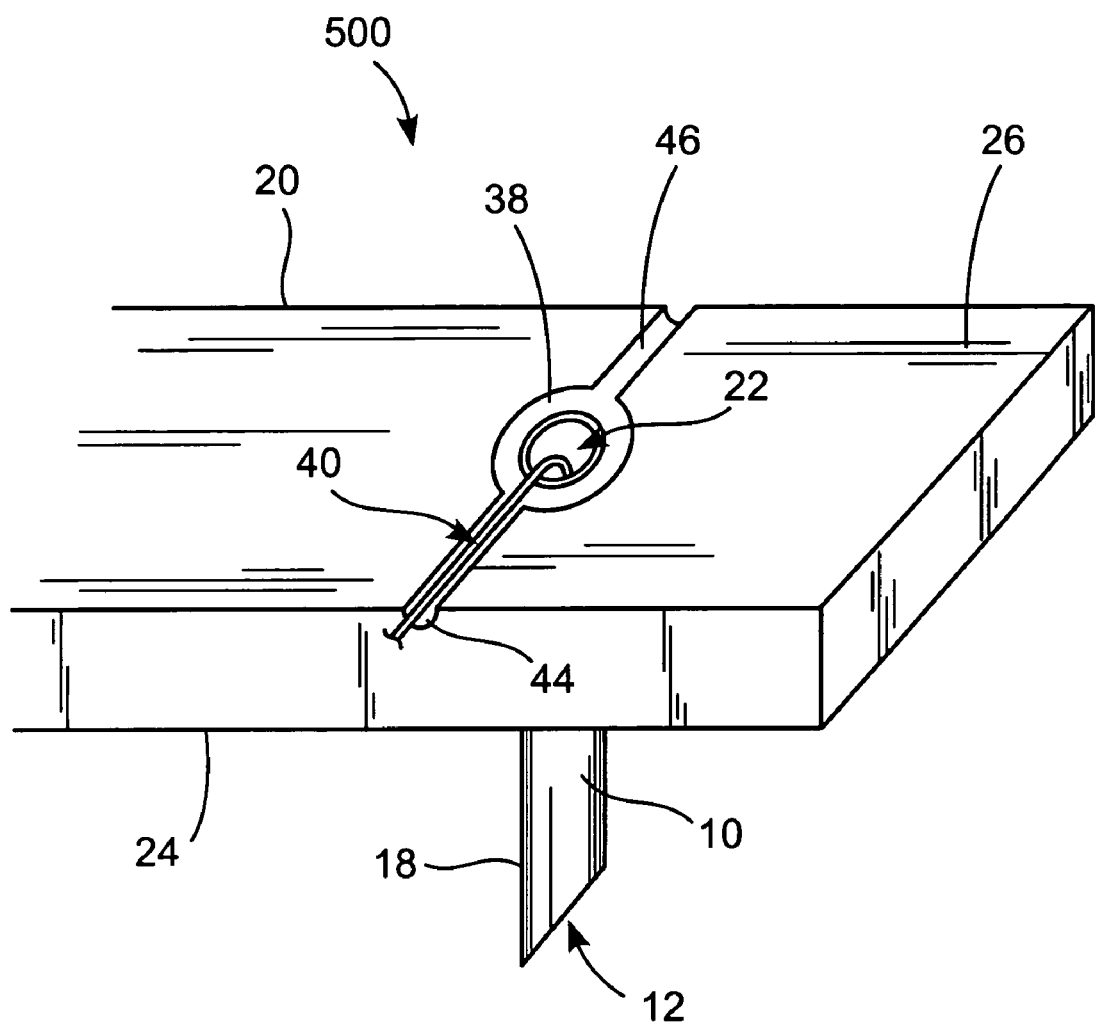
FIG. 8 is a perspective view of still another arrangement formed according to the principles of the present invention.

According to one alternative embodiment, the projection 30 may be formed as a distinct and separate member of the base 20, and may be provided generally in the form of a wire (See, e.g., FIGS. 5, 7 and 8). The wire may likewise be made of any suitable material, such as a metal or polymer material, as described above.

According to a further alternative embodiment, the projection 30, whether integral with the base or formed as a separate member, can be provided with a fluid transport enhancing surface feature, such as a PDMS or a Silwet coating or a surface texturing applied to at least a portion of the surface of projection 30.

The projection 30 is preferably formed from a non-fibrous material. Alternatively, the projection 30 is formed from a relatively non-porous material. The projection 30 may be formed of any suitable material, such as metal or plastic material. According to one alternative embodiment, the projection 30 is formed from a hydrophilic polymer, such as polycarbonate. Forming the projection 30 of such a material provides the added benefit of increased fluid transport capabilities due to the hydrophilic nature of the material.

The projection 30 is provided with a transverse cross-sectional dimension, which is less than the inner diameter of the lumen 16. In other words, the projection 30 occupies some, but not all, of the cross-sectional area defined by the inner lumen 16 of the tube 10 or needle 18. The interaction between fluid traveling within the lumen 16 with the reduced cross-sectional area is believed to provide enhanced capillary action that pulls the fluid further along the path toward the second end 14, and ultimately the second surface 26 of the base 20. The ratio between the cross-sectional area of the lumen 16 and the projection 30 can be varied by changing one or more of the inner diameter of the tube 10 or needle 18, and transverse cross-sectional dimension, or outer diameter, of the projection 30. If the difference in cross-sectional area between the lumen 16 and the projection 30 is too small, no flow will occur due the high resistance to flow caused by a capillary passageway defined by the inner diameter of the lumen and the projection 30 that is too small. The above-described dimensions can be readily varied, and optimized depending upon numerous factors, such as the nature of fluid being transported. When the fluid to be transported is comprised of mainly whole blood, according to one non-limiting example of the present invention, the lumen may be provided with an inner diameter on the order of 0.012 inches, and the projection 30 may be provided with a transverse cross-sectional dimension on the order of 0.0065 inches. It has been observed that an arrangement provided with this construction successfully transports blood samples having volumes ranging from about 200-500 nl.

The projection 30 provides numerous advantages and benefits compared with arrangements with the prior art. For example, the above-described arrangement is operable to transport a sample of fluid having a volume that is insufficient to fill the entire volume of the defined by the lumen 16 of tube 10 or needle 18. The enhanced powerful capillary action created by the projection 30 is believed to facilitate the transfer of volumes of fluid, which are less than the volume of the above-described lumen 16. In addition, the fluid transport mechanism is not dependent upon flow of the fluid through the voids defined within the interior of a porous or fibrous material, which can be time consuming and reduces the volume of fluid available for analysis and may alter the composition of the blood components (i.e., change hematocrit) in unpredictable ways. The enhanced flow that enables transport smaller volumes of fluid advantageously permits working with smaller sample volumes. This is important in certain applications, such as lancing operations to draw a sample of blood from the skin. The ability to utilize smaller sample volumes in turn enables the adoption of lancing techniques that minimize pain and intrusiveness to the patient as well as the potential need for milking of blood from the wound to the surface of the skin. In addition, the ability to transport a smaller sample volume, as well as a lack of dependence upon flow through a porous or fibrous material, also enables a quicker overall transport operation, and in turn, permits a quicker overall testing procedure, which is also advantageous to the user.

Figure 4:
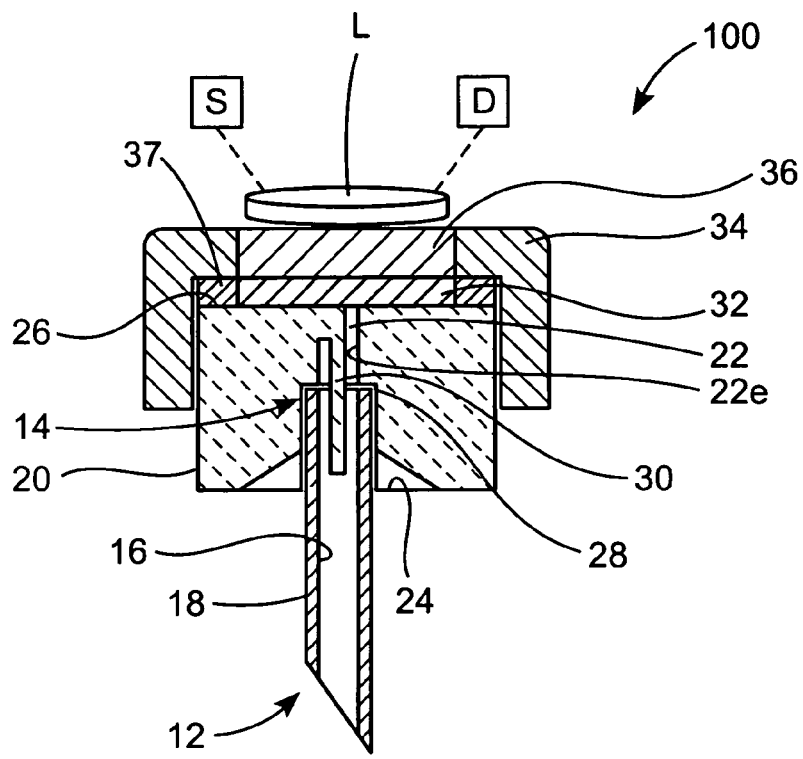
FIG. 4 is a cross sectional view of another arrangement formed according to the principles of the present invention.

The arrangement 100 may further comprise and analyte quantification member 32. The analyte quantification member 32 may be provided in many different forms. In general, the analyte quantification member 32 may be in the form of a member that provides quantification by any suitable technique, such as electrochemical or photometric analysis. According to one exemplary embodiment, the analyte quantification member 32 comprises an assay pad or membrane, which contains one or more chemical reagents selected to react with a predetermined analyte, thereby producing a readable signal. For example, as illustrated in FIG. 4, a typical photometric detection arrangement may be provided for quantification of the analyte contained in the fluid sample being analyzed. According to such arrangements, a light source S, and a detection element D are provided which are in optical communication with the analyte quantification member or membrane 32. One or more optical components such as, one or more lenses L, may optionally be included in the arrangement. As the fluid sample reaches the quantification member or assay pad 32, a reaction occurs between a target analyte and one or more chemical reagents contained within the assay pad 32. This reaction produces a color change in the assay pad 32, which can then be detected and analyzed by the arrangement including the light source S, detection element D, and optional lens L in a manner familiar to those in the art.

According to one embodiment, the analyte quantification member 32 is in fluid communication with the bore 22. According to another embodiment, the analyte quantification member 32 is in direct fluid communication with the bore 22. In other words, there are no additional components or features intervening between the bore 22, which opens at the second surface 26, and at least one surface of the analyte quantification member 32. This arrangement is beneficial in that the fluid may be transported from the lumen 16 and or bore 22 directly to the analyte quantification member 32, thereby enabling a quicker overall fluid transport operation than some arrangements of the prior art, such as those arrangements which include one or more intervening layers between the analyte quantification member 32 and a fluid transport channel or passageway.

The arrangement 100 may further comprise a means for securing the analyte quantification member 32 to the base 20. Suitable means for securing include an adhesive provided between the analyte quantification member 32 and the base 20, one or more recess features provided on the base 20 which trap the quantification member 32 therein, transparent adhesive tape placed over the quantification member 32, or an integral or separate cover member disposed on the base overlying the quantification member 32. One exemplary embodiment of such a cover is illustrated in FIG. 4. In particular, a cap 34 is illustrated, and provides a mechanism for securing the analyte quantification member 32 to the base 20. The cover or cap 34 preferably includes a means for allowing optical communication with the analyte quantification member 32 lying below. Suitable means include forming the cover or cap 34 entirely of a transparent or translucent material, or providing one or more windows 36 of transparent or translucent material in the cover or cap 34 which may be otherwise formed from an opaque material. The cap or cover 34 may be secured to the base 20 by any suitable means. Suitable means include fasteners, a press fit, snaps, latches, adhesives, and thermal bonding. An optional spacer ring 37 may also be provided in order to limit compression of the analyte quantification member 32.

An alternative arrangement 200 of the present invention is illustrated in FIG. 5. Certain selected features of arrangement 200 have been previously described in connection with arrangement 100, and thus are depicted utilizing the same reference numerals as those corresponding features contained in the previously described arrangement. A full description of these common features will not be repeated, however, it should be understood that the entire content of the previous description is incorporated by reference herein. One distinguishing characteristic of the arrangement 200 is that the base 20 is provided with a bore 22 extending from the first surface 24 to the second surface 26, and the second end 14 of the tube 10 or needle 18 is received within the bore 22 such that the second end 14 is substantially co-planar with the second surface 26 with the base 20. In addition, a counter bore 28 is omitted. The fluid transport enhancement projection of the arrangement 200 is optionally provided in the form of one or more wires 40. The wires 40 are formed from any suitable material, such as a metallic or polymeric material. At least a portion of the surface of the one or more wires may be provided with the fluid transport enhancing coating or surface texturing, as previously described herein. The wires extend from the second end 14 or tube 10 or needle 18 downwardly into the lumen 16. The wires may be secured to the base 20. Alternatively, the wires 40 may be trapped between the analyte quantification member 32 and the base 20. Another distinguishing characteristic is the provision of a counter bore 38 within the base 20, which contains the analyte quantification member or membrane 32. The counter bore 38 serves the purpose of providing a means to facilitate securing the analyte quantification member or membrane 32 to the base 20. In addition, the counter bore 38 provides a mechanism by which compression of the analyte quantification member 32 by a cover or cap 34 (e.g., FIG. 4) may be controlled, thereby preventing over compression. In the illustrated embodiment, the counter bore 38 is provided with surfaces that are generally flat and lie at right angles with respect to one another. However, alternative configurations are contemplated. For example, the counter bore 38 may be in the form of a concave surface extending into the base 20. The counter bore 38 could also be convex (not shown).

Figure 6:
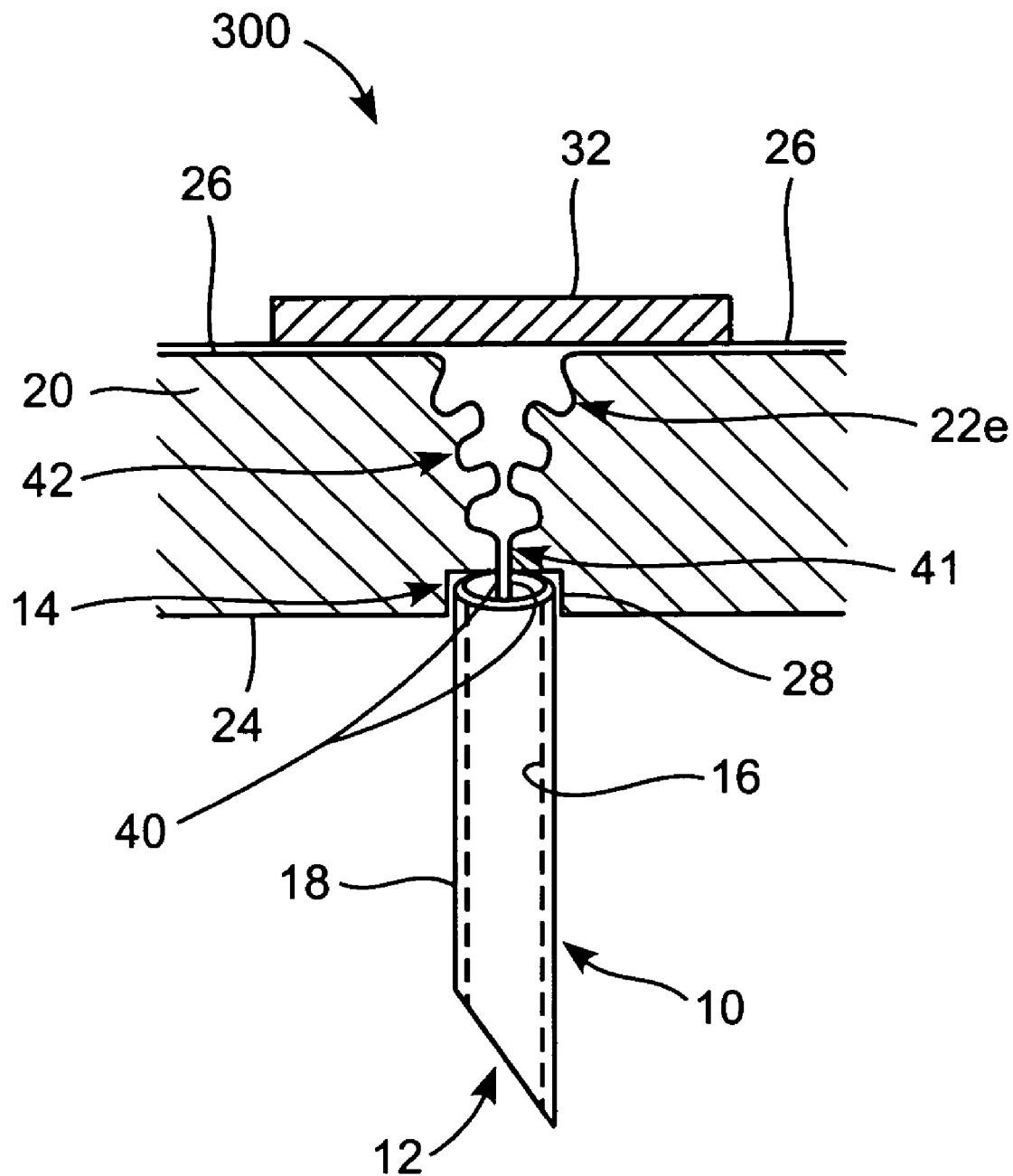
FIG. 6 is a partial cross sectional view of yet another arrangement formed according to the principles of the present invention.

A further alternative arrangement 300 is depicted in FIG. 6. Only those features that distinguish the arrangement 300 from previously described arrangement will be discussed, and the previous discussions of features and arrangements are incorporated by reference herein. In the arrangement 300, the base 20 is provided with a counter bore 28, which receives the second end 14 of tube 10 or needle 18. The bore 22 contained in the base extends beyond the second end of 14 of the tube 10 or needle 18, and through the second surface 26 of the base 20, as indicated at 22e. As illustrated in FIG. 6, the bore 22 may be optionally provided with a throat portion 41 having an inner diameter, which is small than the lumen 16 of the tube 10, or needle 18. This throat acts to further enhance the capillary action at the second end 14 of the tube 10 or needle 18. According to a further embodiment, the portion of the bore 22e may be provided with a fluid transport enhancing feature at least a portion of the surface thereof. For example, that portion of the counter bore 22e extending from the second end 14 to second surface 26 may be provided with a fluid transport enhancement coating or surface texturing as previously described herein. This feature is generally indicated at 42. The arrangement 300 may also include one or more wires 40, or at least one projection (e.g., 30, FIG. 4).

FIG. 7 illustrates yet another alternative arrangement 400 constructed to the principles of the present invention. A full discussion of the features contained in the previously described arrangements are incorporated by reference herein. The arrangement 400 may optionally be provided with a counter bore 38 in the base 20, for receiving the analyte quantification detection member 32 (not shown). One distinguishing characteristic of the arrangement 400 is the inclusion of at least one groove, channel, or depression (hereafter collectively referred to as "groove") 44 formed in the base 20. A projection may optionally be contained within the at least one groove 44, as is in the case in the illustrated arrangement 400. In particular, the projection may be in the form of one or more wires 40 according to the illustrated arrangement 400. The wire 40 may optionally be secured within the at least one groove 44 by any suitable means, such as an adhesive or thermal bonding. The provision of at least one groove 44 provides significant advantages according to the principles of the present invention, and may be included in any of the arrangements described herein. The grooves may have any suitable cross-sectional geometry or configuration. Suitable configurations include square, rectangular, semi-circular, linear, and curved shapes. Similarly, the at least one groove 44 may be provided with any suitable dimensions. For example, square or rectangular grooves may be provided with a depth on the order of 0.002-0.020 inches and a width on the order of 0.002-0.020 inches. Similarly, semi-circular or curved grooves may be provided with a radius of curvature on the order of 0.002-0.022 inches. According to the illustration of embodiment, only one groove 44 is provided. However, it is contemplated that many more grooves may be provided having either the same or different configuration or dimensions. In addition, one or more grooves may extend down into at least portion 22e of the bore 22 (not shown). The provision of at least one groove 44 provides numerous advantages. For example, the at least one groove 44 serves as a means to facilitate the precise location and retention of the projection 30 (see, e.g., FIG. 1) or wire 40. In addition, the at least one groove 44 is in communication with the bore 22 thus, as air that is normally contained in the lumen 16 of the tube 10 or needle 18, is pushed upward of the flow of fluid in the lumen 16, the at lease one groove 44 provides a pathway for venting this air, thus facilitating the flow of fluid up through the lumen, into the bore 22 and ultimately into the analyte quantification member 32. The at least one groove 44 may also be provided, on at least a portion of a surface thereof, with one or more fluid transport enhancing coatings or surface texturing, having those features and characteristics previously described herein. It should be evident that any of the embodiments described herein can include at least one groove 44. For example, the arrangement 100 may include at least one groove in fluid communication with the bore 22, as described above.

Further details concerning the at least one groove 44 are provided in related application Ser. No. 11/239,123, entitled DEVICES AND METHODS FOR FACILITATING FLUID TRANSPORT, filed on even date with the present application, the entire content of which is incorporated by reference herein.

A further alternative arrangement 500 constructed according to the principles of the present invention is depicted in FIG. 8. A complete discussion of all of the features contained in the arrangement 500 is incorporated herein by reference, as previously noted in the discussion of the alternative previously-described arrangements. According to the arrangement 500, a counter bore 38 is optionally provided in the base 20, which house an analyte quantification member or assay pad 32 (not shown). According to the illustrated embodiment, the counter bore 38 is provided as a generally concave surface. The arrangement 500 is also provided with at least one groove 44, which serves to contain the fluid transport enhancing projection or wire 40 therein, and includes all the features and characteristics of that previously described with the arrangement 400. The arrangement 500 further optionally includes at least one additional groove, channel or depression (hereafter "groove") 46 on base 20. The groove 46 may be provided with the same configuration, sizes and fluid transport enhancing features as the previously described groove 44. This additional groove 46 provides the same advantages previously noted in the description of groove 44. In addition, according to the illustrated embodiment, there is no wire 40 or similar projection 30 to be disposed to groove 46, thus it possesses a greater capability for venting air out of the lumen 16 through the bore 22 away from the base 20. Thus, the arrangement 500 may provide for greater venting capability relative to arrangements such as that as arrangement 400 as discussed in connection with FIG. 7. Any of the embodiments described herein may include an additional groove, such as the arrangement 100.

An integrated device for sampling and testing a sample of body fluid for analyte concentration formed according to the principles of the present invention may have a number of suitable configurations. According to certain embodiments the device is configured to perform testing by acquiring a sample of blood from the user, transfer the sample to an analysis site, and determine the concentration of glucose contained therein. These operations are all performed with little or no user input. For example, these operations may commence automatically according to a specified or predetermined schedule. Alternatively, these operations may commence at the command of the user via, for example, pressing a start button on the device.

The device may include disposable and reusable portions. The disposable portion may include at least one skin piercing element/transport member and analysis site (which may include an assay pad). The disposable portion may provide the capability to perform a single test. After testing is complete, the disposable portion is discarded and replaced with a new disposable portion before performing another test. Alternatively, the disposable portion includes a plurality of skin piercing elements/transport members and analysis sites. Such disposable units permit a plurality of tests to be performed before it is necessary to discard and replace the disposable unit. The device may be either wearable or handheld, or both.

Figure 9:
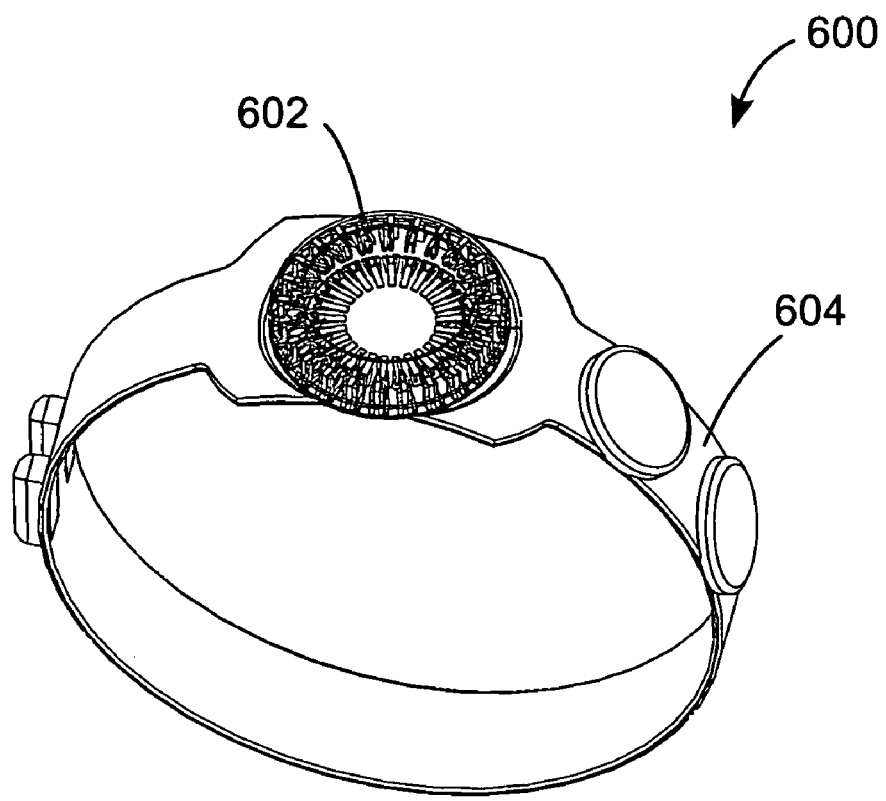
FIG. 9 is a perspective view of a device incorporating any of the arrangements constructed according to the principles of the present invention.
Figure 10:
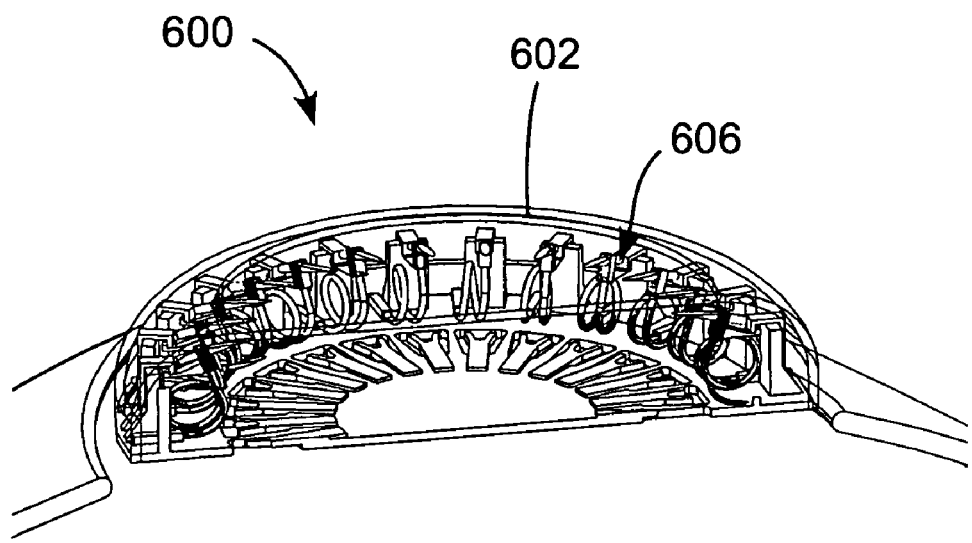
FIG. 10 is a partial cutaway view of the arrangement of FIG. 9.

A non-limiting exemplary integrated device is illustrated in FIGS. 9-10. As illustrated therein the device 600 generally comprises a functional portion 602, and an optional attachment means or band 604. Thus according to the present invention, the integrated device 600 may be wearable. In addition, or alternatively, the integrated device may be operable as a hand-held device. For example, according to the illustrated embodiment, the band 604 can be separated and/or otherwise removed from the user, and the device 600 stored in a suitable case or in the user's pocket. The band can then be grasped and used to hold the device against the skin to perform a testing operation.

The device 600 preferable includes at least one arrangement for performing a measurement of the concentration of an analyte contained in a sample of blood. According to the illustrated embodiment, the device 600 comprises at least one arrangement 606 having features as described herein, including a hub-like base, at least one skin-piercing element, at least one fluid-transport enhancing projection, and at least one analysis site which may contain an assay pad. The at least one arrangement 606 may form part of a disposable portion or unit. According to one embodiment, the disposable unit allows for at least one measurement of the concentration of an analyte contained in a sample of blood prior to being discarded and replaced. According to a further embodiment, the disposable unit allows for a plurality of measurements of the concentration of an analyte contained in a sample of blood prior to being discarded and replaced.

All of the above-described exemplary arrangements of the present invention may be used independently, or in combination with other devices and arrangements, and systems. Inclusion in other types of devices, wearable and non-wearable, are specifically contemplated by the present invention. Additional details of such discrete autonomous integrated testing devices may be gathered from the disclosure of U.S. patent application Ser. No. 60/721,966, entitled DEVICE FOR FLUID ANALYSIS WITH SAMPLE EXTRACTION AND TRANSPORT, the entire content of which is incorporated herein by reference.

According to the present invention, there is also provided methods for improving the transport of fluid. The present invention also provides methods for improving the transport of body fluid within a transport tube or needle by enhancing the capillary transport properties of the lumen of the tube or needle.

According to one aspect, the present invention provides a method of improving transport of a fluid, such as a body fluid, comprising: providing a needle having a first end and a second end opposite the first end, and a lumen having an inner diameter; and introducing at least one fluid transport enhancing projection into the lumen of the needle such that the projection extends from the second end toward the first end.

According to another aspect, the present invention provides a method for improving transport of a fluid, such as a body fluid, comprising: providing a base having a bore disposed therein extending from a first surface of the base through a second surface of the base; providing a fluid transport tube having a first end, a second end opposite the first end, and a lumen having an inner diameter, and introducing at least the second end of the tube within the bore of the base; introducing at least one fluid transport enhancing projection into the lumen of the tube such that the projection extends from the second end toward the first end; and providing an analyte quantification member in fluid communication with the bore.

According to the present invention, any of the above-described methods may further comprise providing the needle with a first end that is constructed for piercing the skin, forming the needle or tube from a metal, and forming the at least one projection from a polymeric material or a metal.

The above-described methods may further comprise extending the bore beyond the second end of the tube or needle, wherein the portion of the bore extending from the second end of the tube or needle to the second surface optionally comprises a fluid transport enhancing feature, such as at least one of a coating and a surface texturing. Alternatively, the second end of the tube or needle is disposed such that it is substantially coplanar with the second surface.

In any of the above-described methods, the at least one projection may be formed as an integral extension of the base. Alternatively, the projection may be formed as a wire.

According to the methods of the present invention, the quantification member is disposed such that it is in direct fluid communication with the bore. The quantification member may be formed of a fibrous membrane containing a chemical reagent chosen to react with a predetermined analyte.

Methods of the present invention may further include providing a cover overlying the quantification member. The cover may be constructed to permit optical communication with the quantification member; for example, the cover may be formed entirely of a transparent or translucent material.

In any of the above-described methods, at least one groove may also be provided in the second surface of the base such that it is in fluid communication with the bore.

According to the methods of the present invention, a wearable or hand held blood glucose monitor can be formed and/or operated by a method comprising, at least in part, any of the above-described methods.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6

We claim:

1. An arrangement comprising:
 a needle comprising a first end and a second end opposite the first end, and a lumen having an inner diameter and a longitudinal length; and
 at least one fluid transport enhancing projection comprising an outer peripheral surface and extending toward the first end;
 wherein the at least one projection extends from the base and is constructed and arranged to enhance fluid transport by enhancing capillary forces drawing fluid along the outer peripheral surface of the at least one projection.

2. The arrangement of claim 1, wherein the first end of the needle is constructed for piercing the skin.

3. The arrangement of claim 1, wherein the needle is formed from a metal, and the at least one projection is formed from a plastic or a metal.

4. The arrangement of claim 1, further comprising a base having a bore disposed therein extending from a first surface of the base through a second surface of the base, and at least the second end of the needle being received by the bore.

5. The arrangement of claim 4, wherein the bore extends beyond the second end of the needle.

6. The arrangement of claim 5, wherein the portion of the bore extending beyond the second end of the needle has an inner diameter that is substantially the same as the inner diameter of the lumen.

7. The arrangement of claim 4, wherein the second end of the needle is disposed such that it is substantially coplanar with the second surface.

8. The arrangement of claim 1, wherein the projection terminates before extending past the second end of the needle and into the lumen, or extends into the lumen and up to 100% of the longitudinal length of the needle.

9. The arrangement of claim 1, wherein the at least one projection comprises an integral extension of the base.

10. The arrangement of claim 1, wherein the at least one projection comprises at least one wire.

11. The arrangement of claim 1, further comprising an analyte quantification member in fluid communication with the bore.

12. The arrangement of claim 11, wherein the quantification member is in direct fluid communication with the bore.

13. The arrangement of claim 11, wherein the quantification member comprises an assay pad containing a chemical reagent chosen to react with a predetermined analyte.

14. The arrangement of claim 12, further comprising a cover overlying the quantification member.

15. The arrangement of claim 14, wherein the cover is constructed to permit optical communication with the quantification member.

16. The arrangement of claim 8, wherein the projection extends past the second end of the needle and into the lumen.

17. An integrated analyte detector device comprising the arrangement of claim 1.

18. The device of claim 17, wherein the device is configured to be wearable or handheld.

19. The device of claim 18, wherein the device is constructed to perform at least one blood glucose concentration measurement.

20. The device of claim 19, wherein the device comprises a disposable cartridge.

21. The device of claim 19, wherein the device is constructed to perform multiple blood glucose concentration measurements.

22. An arrangement comprising:
    a base having a bore disposed therein extending from a first surface of the base through a second surface of the base;
    a fluid transport tube having a first end, a second end opposite the first end, and a lumen having an inner diameter and a longitudinal length, at least the second end of the tube being received within the bore of the base;
    at least one fluid transport enhancing projection comprising an outer peripheral surface and extending toward the first end; and
    an analyte quantification member in fluid communication with the bore;
    wherein the at least one projection extends from the base and is constructed and arranged to enhance fluid transport by enhancing capillary forces drawing fluid along the outer peripheral surface of the at least one projection.

23. The arrangement of claim 22, wherein the projection terminates before extending past the second end of the tube and into the lumen, or extends into the lumen and up to 100% of the longitudinal length of the tube.

24. The arrangement of claim 22, wherein the fluid transport tube comprises a needle and the first end of the needle is constructed for piercing the skin.

25. The arrangement of claim 22, wherein the needle is formed from a metal, and the at least one projection is formed from a plastic or a metal.

26. The arrangement of claim 22, wherein the bore extends beyond the second end of the tube.

27. The arrangement of claim 26, wherein the portion of the bore extending beyond the second end of the tube has an inner diameter that is substantially the same as the inner diameter of the lumen.

28. The arrangement of claim 22, wherein the second end of the tube is disposed such that it is substantially coplanar with the second surface.

29. The arrangement of claim 26, wherein the portion of the bore extending from the second end of the tube to the second surface comprises at least one of a coating and a surface texture.

30. The arrangement of claim 22, wherein the at least one projection comprises an integral extension of the base.

31. The arrangement of claim 22, wherein the at least one projection comprises at least one wire.

32. The arrangement of claim 22, wherein the quantification member is in direct fluid communication with the bore.

33. The arrangement of claim 22, wherein the quantification member comprises an assay pad containing a chemical reagent chosen to react with a predetermined analyte.

34. The arrangement of claim 22, further comprising a cover overlying the quantification member.

35. The arrangement of claim 22, wherein the cover is constructed to permit optical communication with the quantification member.

36. The arrangement of claim 23, wherein the projection extends past the second end of the tube and into the lumen.

37. The arrangement of claim 26, further comprising at least one groove disposed in the portion of the bore extending from the second end of the needle to the second surface.

38. An integrated analyte detector device comprising the arrangement of claim 22.

39. The device of claim 38, wherein the device is configured to be wearable or handheld.

40. The device of claim 39, wherein the device is constructed to perform at least one blood glucose concentration measurement.

41. The device of claim 39, wherein the device is constructed to perform multiple blood glucose concentration measurements.

42. The device of claim 40, wherein the device comprises a disposable cartridge.

43. An arrangement comprising:
    a base having a bore disposed therein extending from a first surface of the base through a second surface of the base;
    a fluid transport tube having a first end, a second end opposite the first end, and a lumen having an inner diameter and a longitudinal length, at least the second end of the tube being received within the bore of the base;
    at least one fluid transport enhancing projection comprising an outer peripheral surface and and extending toward the first end;
    an analyte quantification member in fluid communication with the bore; and at least one fluid transport enhancing feature disposed in the second surface of the base and in fluid communication with the bore;
    wherein the at least one projection extends from the base and is constructed and arranged to enhance fluid transport by enhancing capillary forces drawing fluid along the outer peripheral surface of the at least one projection.

44. The arrangement of claim 43, wherein the projection terminates before extending past the second end of the tube and into the lumen, or extends into the lumen and up to 100% of the longitudinal length of the tube.

45. The arrangement of claim 44, wherein the projection extends past the second end of the tube and into the lumen.

46. An arrangement comprising:
    a needle comprising a first end and a second end opposite the first end, and a lumen having an inner diameter and a longitudinal length;
    at least one fluid transport enhancing projection comprising an outer peripheral surface and extending toward the first end; and a base having a bore disposed therein extending from a first surface of the base through a second surface of the base, and at least the second end of the needle being received by the bore, the bore extends beyond the second end of the needle;

wherein the portion of the bore extending from the second end of the needle to the second surface comprises a fluid transport enhancing feature, the feature comprising at least one of a coating and a surface texture;

wherein the at least one projection extends from the base and is constructed and arranged to enhance fluid transport by enhancing capillary forces drawing fluid along the outer peripheral surface of the at least one projection.

47. The arrangement of claim 46, wherein the bore further comprises a counterbore receiving the second end of the needle therein.

48. The arrangement of claim 46, wherein the projection terminates before extending past the second end of the needle and into the lumen, or extends into the lumen and up to 100% of the longitudinal length of the needle.

49. The arrangement of claim 48, wherein the projection extends past the second end of the needle and into the lumen.

50. An arrangement comprising:
a needle comprising a first end and a second end opposite the first end, and a lumen having an inner diameter and a longitudinal length;
at least one fluid transport enhancing projection comprising an outer peripheral surface and extending toward the first end;
a base having a bore disposed therein extending from a first surface of the base through a second surface of the base, and at least the second end of the needle being received by the bore; and
at least one fluid transport enhancing feature disposed in the second surface of the base and in fluid communication with the bore;
wherein the at least one projection extends from the base and is constructed and arranged to enhance fluid transport by enhancing capillary forces drawing fluid along the outer peripheral surface of the at least one projection.

51. The arrangement of claim 50, wherein the projection terminates before extending past the second end of the needle and into the lumen, or extends into the lumen and up to 100% of the longitudinal length of the needle.

52. The arrangement of claim 51, wherein the projection extends past the second end of the needle and into the lumen.

\* \* \* \* \*